United States Patent [19]

Rheinberger et al.

[11] Patent Number: 4,933,202

[45] Date of Patent: Jun. 12, 1990

[54] METHOD OF IMPROVING THE ADHESION OF PLASTICS TO METALS IN DENTAL PROSTHESES

[75] Inventors: Volker Rheinberger, Vaduz; Peter Wollwage, Mauren; Gerhard Zanghellini, Vaduz, all of Liechtenstein

[73] Assignee: Ivoclar Ag, Schaan, Liechtenstein

[21] Appl. No.: 298,952

[22] Filed: Jan. 19, 1989

Related U.S. Application Data

[63] Continuation of Ser. No. 132,355, Dec. 11, 1987, abandoned.

[30] Foreign Application Priority Data

Dec. 11, 1986 [DE] Fed. Rep. of Germany ....... 3642290

[51] Int. Cl.$^5$ .............................................. B05D 3/04
[52] U.S. Cl. ...................... 427/2; 427/307; 427/327; 427/387; 427/388.1; 427/397.7; 427/409
[58] Field of Search ................ 427/2, 397.7, 409, 387, 427/388.1, 327

[56] References Cited

U.S. PATENT DOCUMENTS 3,657,003 2/1970 Kenney ................................ 204/30
4,243,721 3/1979 Baney et al. ......................... 428/412

FOREIGN PATENT DOCUMENTS 1536238 6/1977 United Kingdom .
2082478 8/1981 United Kingdom .

*Primary Examiner*—Bernard Pianalto
*Attorney, Agent, or Firm*—Waldron & Associates

[57] ABSTRACT

In a process for improving the adhesion of plastics to metals in the production of dental prostheses, in which a silicon dioxide layer is applied to the metal surface and subsequently silanized and then the plastic and metal bonded together the improvement consisting essentially of, forming the silicon dioxide layer by (1) applying a silica sol or dispersion of very finely divided silica to the metal surface and (2) baking the sol or dispersion at a temperature of 100° to 800° C.

15 Claims, No Drawings

METHOD OF IMPROVING THE ADHESION OF PLASTICS TO METALS IN DENTAL PROSTHESES

This is a continuation application of application Ser. No. 135,355, filed Dec. 11, 1987, now abandoned.

BACKGROUND OF THE INVENTION

The invention relates to a process for improving the adhesion of plastics to metals, particularly in the production of dental prostheses.

A process for applying a crown veneering to a metal prosthesis is known from German Offenlegungsschrift No. 32 11 123. The metal body is immersed once or several times in a silane solution and then dried. Onto the thus obtained silane layer is uniformly thinly applied a prosthesis plastic and subsequently the veneering shell produced according to known processes is pressed on, i.e. the prosthesis plastic is completely polymerized. Prior to silanization of the metal body, which is performed in an ultrasonic bath, the metal body is roughened by sandblasting. The disadvantage of this procedure is that it is only possible to use Si-containing base metal alloys and only ceramic veneering shells.

U.S. Pat. No. 4,364,731 discloses an adhesive layer of inorganic oxides, including silicon dioxide. This oxide layer is silanized and the veneering material is applied by known processes. The inorganic oxide layer is applied to the metal surface by using a sputtering apparatus. This process, requires an extremely accurate procedure for producing an undamaged jacket layer of inorganic oxides. Other processes proposed in this patent specification consist of coating from the vapor phase accompanied by chemical decomposition (CVD process) and plating using reactive ions.

German patent No. 34 03 894 relates to a modification of the procedure of the U.S. patent, which comprises applying the silicon dioxide layer with the aid of a flame hydrolysis burner using a gaseous, oxidizable silicon compound.

The aforementioned prior art processes are either only intended for specific material combinations used in dental prosthesis technology, or they require complicated and expensive apparatus not normally available in dental laboratories, and also an excellent controll of the process for obtaining an optimum adhesive layer. It is therefore necessary to precisely adhere to certain conditions, such as the spacing of the flame hydrolysis burner or sputtering apparatus with respect to the workpiece, e.g. the metal dental prosthesis.

OBJECTS OF THE INVENTION

The object of the present invention is to provide a process for the production of an adhesive layer for plastic/metal, which does not suffer from the aforementioned disadvantages and which can be easily performed without great apparatus expenditure. It is a further object of the invention to counteract the marginal gap appearing over a period of time between the metal and the plastic as a result of different expansion coefficients leading to unattractive discoloration, and to produce a non-detachable connection between metal and plastic.

SUMMARY OF THE INVENTION

The invention therefore relates to a process for improving the adhesion of plastics to metals, particularly in connection with the production of dental prostheses, in which a silicon dioxide layer is applied to the metal surface and then silanized, the process being characterized in that the silicon dioxide layer is provided by applying of a silica sol or a dispersion of a very finely divided silica to the metal surface and then baking at a temperature of 100° to 800° C.

The process of the invention has several important advantages:

Following sandblasting a silica sol in water is brushed onto the surface of metal pieces for crowns or bridges in thin layer form followed by drying and baking at temperatures of 100° to 800° C.

The aqueous silica sol is a stable, non-sedimenting suspension, which is commercially available.

The silica sol or a silica dispersion can also be prepared from very finely divided silica, e.g. pyrogenic fumed silica and $H_2O$.

The process requires neither a sputtering apparatus nor a flame hydrolysis burner for applying the silicon dioxide particles and instead it is merely necessary to have the ceramic oven found in any dental laboratory for baking purposes.

All other processes using ceramic materials require
(a) alloys which are compatible with ceramics and
(b) burning temperatures, which are above the temperature admissible for crown and bridge alloys.

DETAILED DESCRIPTION OF THE INVENTION

The silica sols used according to the invention are aqueous, colloidal dispersions of amorphous silica. The silica is present in the form of non-crosslinked, spherical individual particles which have hydroxyl groups on the surface. The silica sols are homogeneous, non-separating, low viscosity liquids, which can be handled without constituting a health hazard.

Commercially available silica sols contain silica with an average primary particle size between 5 and 150, particularly 5 and 50 nm. The specific surface area (BET) of the silicas is between approximately 50 and 700 $m^2/g$. Silica sol types with a surface area of 200 to 300 $m^2/g$ are generally preferred because it has been found that with the aid thereof an optimum adhesion between metal and plastic can be obtained.

In place of silica sols, it is also possible to use dispersions of very finely divided silica in water and/or alcohol as the dispersant. Pyrogenic (fumed) silicas with an average primary particle size of 5 to 50, particularly 5 to 10 nm and a specific surface area (BET) of 50 to 400 $m^2/g$ are particularly suitable. Such dispersions can also be prepared immediately prior to use in a conventional manner using special stirrers, e.g. a POLYTRON stirrer which produce high shear forces. It is advantageous for this purpose to add stabilizers, such as inorganic fluorine compounds, preferably $K_2ZrF_6$, in order to prevent settling and thickening.

Following the application of the sol or dispersion to the surface of the metal pieces the water and/or alcohol is removed by drying, so that a silica layer is obtained. By baking at temperatures of 100° to 800° C., preferably 300° to 800° C., the layer is firmly anchored to the metal surface. The baking time is generally approximately 2 to 20 minutes, preferably 3 to 10 minutes. Normally the lower the stoving temperature, the longer the stoving time. Surprisingly at these low baking temperatures a kind of sintering takes place, although the melting point of $SiO_2$ is above 1700° C. Contrary to the hitherto held assumptions there is no need to apply the layer by sputtering or flame hydrolysis in order to achieve an adequate bond with the metal substrate. It has in fact been found that the oxide layers produced according to the invention at lower temperatures have a higher elasticity and are therefore better able to follow thermally caused dimension changes of the metal, without there being any peeling off and cracking.

Silanization of the stoved oxide layer is carried out in conventional manner. Preferred silanes are e.g. vinyl-trimethoxysilane, N-β-(N-vinylbenzylamino)-ethyl- γ-aminopropyltrimethoxysilane, γ-methacryloxypropyl-trimethoxysilane, γ-glycidyloxypropyltrimethoxysilane, etc. These compounds are preferably used in the form of alcoholic or acetic acid solutions.

The following examples serve to further illustrate the invention and show by means of model tests that the very simple method of the invention surprisingly leads to an extremely strong bond between the metal substrate and the plastic used for veneering purposes.

EXAMPLE 1

Various silica sols are thinly applied to a small plate (10×20×1 mm) of a base metal alloy. The latter is a dental cobalt-chromium alloy. The plates are sandblasted prior to the application of the silica sols. Following coating the plates are dried and then stoved for 5 minutes at 400° C. in an oven for dental ceramics (Programat). This leads to a vitreous layer, which is silanized. The silanizing agent used is a 10% γ-methacryloxypropyltrimethoxysilane solution. Silanization is followed by the application of a thin, opaque plastic layer essentially comprising a fluid mixture of methylmethacrylate and an opaque methylmethacrylate polymer and this is dry polymerized for 10 minutes at 120° C. This leads to a firm plastics coating, which has on the surface a thin lubricating coating of non-polymerized material.

On the small plates are placed small metal tubes having an internal diameter of 5 mm. Into the metal tubes is pressed a hot polymerizable crown and bridge material (approximately 40% reaction product of hydroxyethyl-methacrylate and trimethylhexamethylene diisocyanate mixed with fumed silica) and completely polymerized. The metal tube is removed and a small metal plate is obtained with the initially polymerized plastic cylinder, which has a diameter of 5 mm and a height of 5 mm. After storing in water for one hour at 37° C., the shear strength is measured. The plate is fixed for this purpose and the plastic cylinder is loaded with a wedge at a distance of 0.5 mm from the plate. The thrust is 0.8 mm/min and loading takes place up to break. A plate without silica sol and silanization is used for comparison purposes.

Table 1 shows the silica sols used and Table 2 the shear strength values obtained. Silica sols A, B, C, D and E are commercially available (e.g. from Bayer AG), whilst dispersion F is prepared by homogeneously mixing 20 g of microfine (fumed) silica (pyrogenic silica AEROSIL 200 from Degussa AG) with 1 g of $K_2ZrF_6$ and 80 g of distilled water in a mixer with high shear forces (POLYTRON).

TABLE 1

| | Silica sols | | | | |
|---|---|---|---|---|---|
| | A | B | C | D | E |
| Solid content % | 30 | 40 | 30 | 30 | 30 |
| $Na_2O$ content % | 0,15 | 0,4 | X | 0,35 | X |
| pH-value | 10 | 10 | 9.3 | 9.8 | 9.1 |
| Density g/cm³ | 1.2 | 1.29 | 1.2 | 1.21 | 1.2 |

TABLE 1-continued

| | Silica sols | | | | |
|---|---|---|---|---|---|
| | A | B | C | D | E |
| Viscosity mPa.s | 2–3 | 7–10 | 3–6 | 3–6 | 3–4 |
| Specific surface m²/g | 100 | 200 | 300 | 300 | 200 |
| Average primary particle size nm | 25–30 | 15–20 | 7–8 | 7–8 | 15–20 |
| Ion type | a. | a. | a. | a. | a. |

X = stabilized with $NH_3$
a. = anionic

TABLE 2

| Shear strength in N/mm² | |
|---|---|
| Silica sol | |
| A | 11.2 ± 2.5 |
| B | 9.9 ± 1.9 |
| C | 13.3 ± 1.8 |
| D | 13.5 ± 2.3 |
| E | 13.0 ± 2.4 |
| F | 8.1 ± 2.3 |
| comparison example (without silica sol) | 4.0 ± 1.2 |

The present process clearly significantly improves the adhesion of the plastic to the metal.

EXAMPLE 2

Example 1 is repeated with different precious metal alloys. Use is made of so-called economic alloys, which have as their main components silver and palladium. The shear strength values are given in Table 3 in N/mm² for 3 silica sols on different alloys.

TABLE 3

| | Shear strength N/mm² | | | |
|---|---|---|---|---|
| | Comparison without silica sol | C | D | E |
| Alloy 1 | 3.3 ± 1.3 | 7.2 ± 1.6 | 6.8 ± 1.1 | 7.6 ± 1.7 |
| Alloy 2 | 3.3 ± 0.7 | 5.2 ± 2.7 | 7.0 ± 2.5 | 6.3 ± 1.6 |
| Alloy 3 | 2.9 ± 0.6 | 7.4 ± 2.8 | 7.8 ± 3.3 | 5.9 ± 0.9 |

Here again the bond between the plastic and metal is significantly improved by the use of silica sols as adhesives according to the present invention.

What we claim is:

1. In a process for improving the adhesion of plastics to metals in the production of dental prostheses, in which a silicon dioxide layer is applied to the metal surface and subsequently silanized and then the plastic and metal bonded together the improvement consisting essentially of, forming the silicon dioxide layer by (1) applying a silica sol or dispersion of very finely divided silica to the metal surface and (2) baking the sol or dispersion at a temperature of 100° to 800° C.

2. Process according to claim 1, characterized in that a baking temperature of 300° to 800° C. is used.

3. Process according to claim 1, characterized in that a baking time of 2 to 20 minutes is chosen.

4. Process according to claim 1, characterized in that the metal surface is pretreated by sandblasting.

5. Process according to claim 1, characterized in that use is made of a silica sol with an average primary particle size of 5 to 150 nm.

6. Process according to claim 1, characterized in that a silica dispersion with an average primary particle size of 5 to 50 nm is used.

7. Process according to one of the claims 1 to 5, characterized in that water and/or alcohol is used as the dispersant for the silica sol or dispersion.

8. Process according to one of the claims 1 to 6, characterized in that inorganic fluorine compounds, particularly $K_2ZrF_6$ are used for stabilizing the silica dispersion.

9. A process for bonding plastic to metal in the production of dental prosthesis, the steps consisting essentially of:
   a. sandblasting the metal surface to be bonded to plastic;
   b. forming a silica sol or a dispersion of very finely divided silica;
   c. applying the sol or dispersion to the sandblasted metal surface to form a coating of the sol or dispersion thereon;
   d. baking the sol or dispersion coating at a temperature 100° to 800° C.;
   e. silanizing the baked silica coating; and
   f. bonding the plastic to the metal surface.

10. A process according to claim 9 wherein the baking temperature is from 300° to 800° C.

11. A process according to claim 9 wherein the baking time is from 2 to 20 minutes.

12. A process according to claim 9 wherein a silica sol is utilized having an average primary particle size of 5 to 150 nm.

13. A process according to claim 9 wherein a silica dispersion is utilized having an average primary particle size of 5 to 50 nm.

14. A process according to claim 9 wherein water and/or alcohol is used as the dispersant for the silica sol or dispersion.

15. A process according to claim 9 wherein inorganic fluorine compounds, particularly $K_2ZrF_6$ are used for stabilizing the silica dispersion.

* * * * *